United States Patent [19]

Simpson et al.

[11] 4,135,981
[45] Jan. 23, 1979

[54] DEVICE FOR RECOGNITION AND DIFFERENTIATION OF GROUP D STREPTOCOCCI

[75] Inventors: Lynn B. Simpson, Corning; Milton M. Takeguchi, Painted Post, both of N.Y.

[73] Assignee: Corning Glass Works, Corning, N.Y.

[21] Appl. No.: 791,549

[22] Filed: Apr. 27, 1977

[51] Int. Cl.² .......................... C12K 1/06; C12K 1/10
[52] U.S. Cl. ......................... 195/127; 195/103.5 M
[58] Field of Search ........ 195/103.5 M, 127, 103.5 R, 195/100, 139, 99

[56] References Cited

U.S. PATENT DOCUMENTS

| 3,830,702 | 8/1974 | Beckford | 195/139 |
| 3,830,703 | 8/1974 | Beckford | 195/127 |
| 3,832,288 | 8/1974 | Rollender et al. | 195/139 |

OTHER PUBLICATIONS

Blazevic et al., *Principles of Biochemical Tests in Diagnostic Microbiology*, John Wiley & Sons, New York, (1975), pp. 41-43, and 59-61.
Facklam, "Comparison of Several Laboratory Media for Presumptive Identification of Enterococci and Group D Streptococci," *Applied Microbiology*, vol. 26, No. 2, (1973), pp. 138-145.
Facklam, "Streptococci," *Manual of Clinical Microbiology*, 2nd ed., Chapter 8, Lennette et al. Ed., American Society for Microbiology, Washington, D.C., (1974), pp. 104-106.

*Primary Examiner*—Thomas G. Wiseman
*Attorney, Agent, or Firm*—William E. Maycock; Clinton S. Janes, Jr.; Clarence R. Patty, Jr.

[57] ABSTRACT

Device for simultaneous recognition of group D streptococci and the differentiation of members of that group into enterococci and nonenterococci bacteria. Device comprises an elongated substantially cylindrical transparent tube having upper and lower chambers joined by a conduit having a smallest diameter smaller than either chamber. The upper chamber contains a semi-solid bile-esculin medium capable of indicating the presence of group D streptococci. The lower chamber contains a semi-solid enterococci distinguishing medium having a NaCl content of at least about 6.5%. Media in the two chambers are separated by a gas (e.g., air) within the conduit.

4 Claims, 2 Drawing Figures

Bile-esculin medium 6.5% NaCl medium (a)  (b)  (c)  (d)  (e)

DEVICE FOR RECOGNITION AND DIFFERENTIATION OF GROUP D STREPTOCOCCI

RELATED APPLICATION

Patent application Ser. No. 791,550, now abandoned, filed of even date in the names of L. Simpson and M. Takeguchi assigned to the same assignee as this application, and entitled, "Rapid Recognition and Differentiation of Group D Streptococci".

BACKGROUND OF THE INVENTION

1. Field:

This disclosure is concerned generally with the field of microbial identification and specifically with a microbial testing device which permits the convenient recognition and differentiation of group D streptococcal bacteria.

2. Prior Art:

Steptococcal bacteria may be conveniently classified according to serological groupings. In a system described by R. Lancefield, the groups are designated by letters of the alphabet. One such group classified according to that system is known as group D streptococci. That group can be conveniently sub-divided into two categories of bacteria, the enterococci and the non-enterococci. See, for example, W. R. Bailey et al., The Streptococci, including the enterococci and anaerobic streptococci, *Diagnostic Microbiology*, 4th Ed., C. V. Mosby Co., pp 122-3 (1974), and R. R. Facklam, Streptococci, *Manual of Clinical Microbiology*, 2nd Ed., ASM, pp. 104-6 (1974).

The differentiation of these two categories is of clinical significance as the enterococci are penicillin-resistant whereas the non-enterococci are penicillin-susceptible. Incorrect or delayed identification of these bacteria could lead to improper antibiotic therapy. Therefore, the rapid and accurate recognition and differentiation of group D streptococci is of definite importance to the physician and patient.

Currently, two physiological characteristics are used routinely to recognize and differentiate the group D streptococci. These methods are disclosed in detail in the above references. Briefly, members of the group are recognized by their ability to hydrolyze esculin in the presence of bile (e.g. 4% oxgall). Hydrolysis can be visually recognized by incorporating ferric ions in the bile-esculin medium. As hydrolysis proceeds, the medium changes from brown to black due to the presence of the ferric ions. The enterococci sub-group can be differentiated from the non-enterococci by the growth of the former in a growth medium containing about 6.5% NaCl. A typical growth medium is prepared by incorporating a nutrient such as dextrose and a pH sensitive color indicator (e.g. bromcresol purple) into the high NaCl medium. As growth proceeds, the dextrose is converted to by-products which cause a pH (and color) change in the medium.

It is well known that bacterial identification systems can be based on devices which provide a variety of selected growth media each of which, because of its constituents, is capable of indicating the presence or absence of a given characteristic. Thus, by incubating a sample of a microbe on a variety of selected media, noting such features as color change, gas evolution, etc., and then comparing those features with those obtained with known organisms, it is possible to identify the sample microbe. See, for example U.S. Pat. No. 3,830,703 (Enteric Bacilli Differentiation) and U.S. Pat. No. 3,830,702 (Bacteriological Media Tube) both of which are concerned with the use of constricted test tubes to contain two or more bacterial identification growth media.

We have now found that by carefully modifying known techniques for identifying group D streptococci and by carefully combining those features with the identification device disclosed in U.S. Pat. No. 3,830,702, there is made available a new device which makes possible an inexpensive, simple, and accurate method for the relatively rapid recognition and differentiation of group D streptococci. Details of our device and preferred ways of making and using it are described herein.

SUMMARY OF THE INVENTION

Our device for the simultaneous recognition and differentiation of group D streptococci comprises a substantially cylindrical transparent test tube having upper and lower chambers separated by a connecting conduit of smaller inner diameter than either chamber, the upper chamber containing a semi-solid bile-esculin medium capable of indicating the presence of group D streptococci, the lower chamber containing a semi-solid enterococci identifying medium having a NaCl content of at least about 6.5%, and the media of two chambers separated by a gas such as air within the conduit. In use, an unknown microbe sample or a sample suspected of being a group D streptococci is placed in contact with each media which are then simultaneously incubated. Group D streptococci may be then recognized and, if present, differentiated on the basis of color changes or lack thereof in the media. The device is simple to use, quite economical and very accurate.

SPECIFIC EMBODIMENTS

Figure 1:
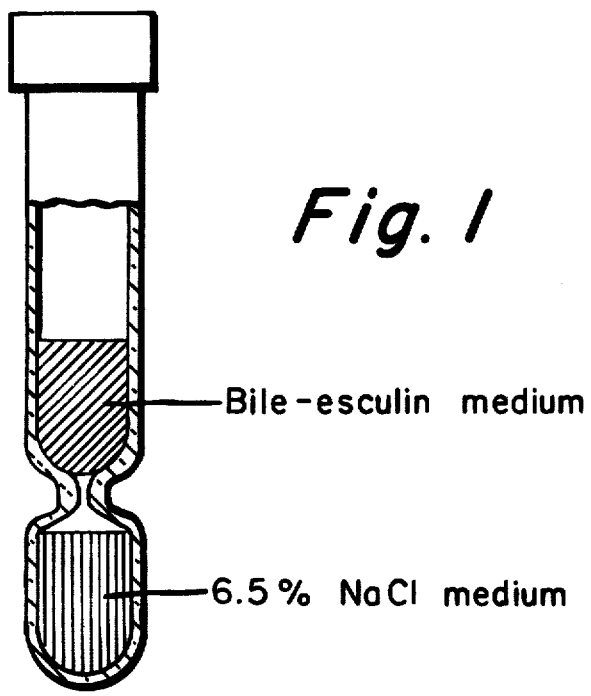
FIG. 1 is a cross sectional view of the bacteriological media device of the present invention.

One configuration of our test device is illustrated in FIG. 1 where there is shown a constricted transparent test tube having both upper and lower chambers each containing test medium which are kept separate by an intermediate conduit (constriction) of reduced cross sectional area (or diameter). As in U.S. Pat. No. 3,830,702, the size or diameter of the conduit is somewhat critical in that it must be large enough to permit the passage of a bacteriological needle containing specimen. The needle is introduced into the lower medium by simply stabbing the needle through the upper medium and the constriction conduit. The conduit must be small enough to keep the upper semi-solid medium from sagging or falling through and mixing with the lower medium. As in the bacteriological media tube in U.S. Pat. No. 3,830,702, the smallest diameter of the passageway or conduit connecting the upper and lower chambers should be between about 1.6 and 2.4 mm.

To assure accuracy with our test device, it was found that the NaCl medium must be in the lower chamber and the bile-esculin medium (BEM) must be in the upper chamber. In initial work, it had been thought that if the NaCl medium had been placed in the bottom position the brown colored reaction product of the BEM might diffuse downward and mask the results in the NaCl medium (red to yellow, a "lighter" color change). For that reason, it was thought to be more practical to place the NaCl medium in the top position and the BEM in the lower position. However, it was soon noted that when the tubes with the NaCl medium in the top position were placed in a $CO_2$ atmosphere, false positive reactions were observed in the NaCl medium. Also a few false negative reactions on the BEM medium were noted. Surprisingly, it was found that by reversing positions and putting the NaCl medium in the bottom chamber and the BEM in the top chamber, false negatives on the BEM and false positives on the NaCl medium were eliminated. Thus, the reversed tubes could be used in a $CO_2$ or non-$CO_2$ atmosphere with no adverse effects. As shown below (Table I), significant downward diffusion of the top medium into the bottom medium was not evident as reactions of the NaCl were not affected. Also, visual examination revealed no discernable physical defects (or diffusion) after 2 weeks.

In the examples below, the tubes used were 13 mm × 100 mm glass constricted tubes having upper and lower chambers (about 3 ml volumn each) separated by a passageway (conduit) of reduced cross-sectional area (about 1.6 mm to 2.4 mm) at the smallest inner diameter. These tubes, which can be made of any transparent material (e.g. glass or plastic) were substantially identical to those described in U.S. Pat. No. 3,830,702.

Although the media in both chambers must be a semi-solid gel-like state, for purposes of filling the tube, the media, especially the lower medium, may be warmed to a liquid state and then injected into the lower portion by means of a needle extending through the constricted passageway. Because of the arcuate shape of the passageway (also in U.S. Pat. No. 3,830,702), potentially trapped air is readily forced passed the needle into the atmosphere during the filling step. After about 1.5 ml of the NaCl medium is placed in the lower portion, the upper portion is partially filled with about the same amount of the bile-esculin medium preferably in a substantially liquid form during the filling step.

Alternatively, the tubes may be filled (using an autoclave) as follows:

Initially the NaCl medium (1.5 ml volume) is placed in the upper chamber of the constricted tubes, and all tubes are covered with aluminum foil. Then, these tubes with the NaCl medium are autoclaved for 15 minutes at 15 psi. Autoclaving creates a vacuum in the lower chamber of these tubes, and when the autoclave is opened, the NaCl medium is drawn from the top chamber into the lower chamber. The tubes are then removed, and the NaCl medium, now in the bottom portion of the tube, is allowed to cool and harden. Then, the warmed sterile bile-esculin medium is pipetted into the top portion of the tube using aseptic techniques. This procedure should be done under a bacteriological hood, if possible. Sterile caps are placed on the tubes and the bile-esculin medium (top portion) is allowed to cool.

The bacteria samples used in the examples below were taken from stock culture collections which had been previously characterized. All bacteria samples were grown on Blood Agar (BA) for 18-20 hours at 35° C. before being tested. The actual medium (BA) used was Heart Infusion agar (Difco, Detroit, Mich.) containing 5% difibrinated sheep blood.

Test Media: The bile-esculin medium used in the examples consisted of the following ingredients:

| Ingredient | Amount (g/l of water) |
| --- | --- |
| PPLO Broth | 21 |
| Agar | 15 |
| Esculin | 1 |
| Ferric Ammonium Citrate | 0.5 |
| Oxgall | 40 |
| The NaCl medium consisted of the following ingredients: | |
| PPLO Broth | 21 |
| Agar | 15 |
| NaCl | 65 |
| Dextrose | 10 |
| Phenol Red | 0.014 |

The NaCl medium (about 1.5 ml) was placed into the lower chamber using the autoclave method and allowed to gel into a reddish, semi-solid mass. The BEM was warmed to about 50° C. and carefully pipetted into the upper chamber and also allowed to gel. All tubes were capped with screw caps. Unless otherwise indicated, all tubes were stored at 4° C. until used.

Five representative bacterial samples were tested using our two-compartment tubes. Tests were done 1 day, 1 week, and 2 weeks after tube preparation and storage at an elevated temperature of 35° C. and no diffusion or mixing of media was observed. The results are summarized in Table I below.

TABLE I

| Sample | Reactions After Storage of Tubes at 35° C. for a period of: | | |
| --- | --- | --- | --- |
| | 1 day | 1 week | 2 weeks |
| Enterococci FM 5797 | +/+ | +/+ | +/+ |
| Non-Enterococci CDC SS 963 | +/− | +/− | +/− |
| S. pyogenes ATCC 10389 | −/− | −/− | −/− |
| Group B Strept OSU-15 | −/− | −/− | −/− |
| α-Strept LBS-1 | −/− | −/− | −/− |
| Uninoculated Control Tube (Stored at 4° C.) | −/− | −/− | −/− |

Reactions recorded as BEM reaction/NaCl medium reaction

In further studies, a shipment of 37 strains of streptococcal bacteria from a University collection were coded as unknown by one person and tested by another using both the tubes of this disclosure and other conventional media. It was found that all group D streptococcal bacteria were identified correctly except for one non-enterococcal strain which was also missed by all other conventional media.

In all of the tests the incubation times were 18-20 hours at 35° C. Although this is longer than the rapid 4 hours incubation times described in our copending patent application Ser. No. 791,550 filed of even date (using lyophilized media), it is thought that in some cases, the convenience of our single tube would justify a slightly longer incubation time. It should be noted, however, that even our 18-20 hr. incubation time compares favorably with present group D streptococcal identification techniques.

Our tubes were found to have excellent shelf life when stored at 4° C. as indicated in the studies summarized by Table II.

TABLE II

Shelf-Life Studies of Solidified Media in Constricted Tube

| Control Cultures | Media Reactions* at Week: | | | | | | | | |
|---|---|---|---|---|---|---|---|---|---|
| | 0 | 2 | 4 | 7 | 8 | 10 | 12 | 15 | 17 |
| Enterococci FM 5797 | +/+ | +/+ | +/+ | +/+ | +/+ | +/+ | +/+ | +/+ | +/+ |
| Non-Enterococci CDC SS 963 | +/− | +/− | +/− | +/− | +/− | +/− | +/− | +/− | +/− |
| S. pyogenes ATCC 10389 | −/− | −/− | −/− | −/− | −/− | −/− | −/− | −/− | −/− |
| Group B Strept OSU-15 | −/− | −/− | −/− | −/− | −/− | −/− | −/− | −/− | −/− |
| α-Strept LBS-1 | −/− | −/− | −/− | −/− | −/− | −/− | −/− | −/− | −/− |
| Uninoculated Control Tube | −/− | −/− | −/− | −/− | −/− | −/− | −/− | −/− | −/− |

*Reactions recorded as BEM reactions/NaCl reactions

Figure 2:
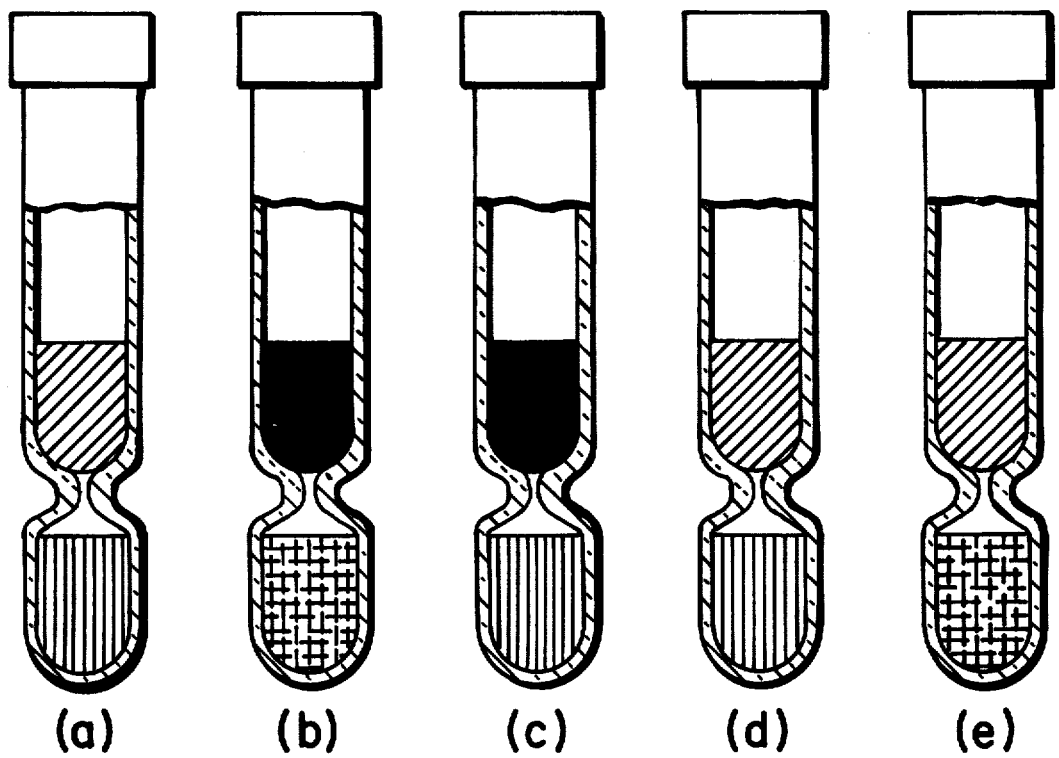
FIG. 2 illustrates the possible combinations of colors in the media of the tube of FIG. 1. These combinations are used to interpret test results.

All possible results that can be obtained using our tubes are illustrated in FIG. 2. The possible combinations of results (color changes) are summarized as follows (See FIG. 2).

TABLE III

| Test Tube | Colors (top/bottom) | Interpretation |
|---|---|---|
| (A) | Brown/Red (−/−) | Uninoculated |
| (B) | Black/Yellow (+/+) | Group D, enterococci |
| (C) | Black/Red (+/−) | Group D, Non-enterococci |
| (D) | Brown/Red (−/−) | Non-Group D |
| (E) | Brown/Yellow (−/+) | Non-Group D |

In subsequent tests to determine if any adverse effects from expected handling and shipping could be expected, a number of uninoculated tubes (about 25), were shipped via U.S. Mail to another testing lab about 250 miles distant. In subsequent tests using the tubes, no adverse effects were noted.

Given the information described herein, it is thought that various modifications will occur to those skilled in the art (e.g., changing the indicator dyes in the BEM or salt medium). Accordingly, it is intended that the above described examples should be considered as merely illustrative and that the scope of the invention disclosed should be limited only by the following claims.

We claim:

1. A device for the simultaneous recognition and differentiation of Group D streptococcal bacteria, the device comprising a substantially cylindrical transparent test tube having upper and lower chambers separated by a connecting conduit of smaller inner diameter than either chamber, the upper chamber including a semi-solid bile-esculin medium capable of indicating the presence of group D streptococcal bacteria, and the lower chamber including a semi-solid enterococci identifying medium having a NaCl content of at least about 6.5% and separated from the medium of the upper chamber by a gas within the connecting conduit.

2. The device, as claimed in claim 1, wherein the smallest connecting conduit diameter ranges from about 1.6 to 2.4 mm.

3. The device, as claimed in claim 1, wherein the test tube is formed of glass.

4. The device, as claimed in claim 1, wherein the test tube is formed of plastic.

* * * * *